US006665373B1

(12) United States Patent
Kotowski et al.

(10) Patent No.: US 6,665,373 B1
(45) Date of Patent: Dec. 16, 2003

(54) X-RAY IMAGING SYSTEM WITH ACTIVE DETECTOR

(75) Inventors: Andreas F. Kotowski, Rancho Palos Verdes, CA (US); Steven W. Smith, Poway, CA (US)

(73) Assignee: Rapiscan Security Products (USA), Inc., Hawthorne, CA (US)

( * ) Notice: Subject to any disclaimer, the term of this patent is extended or adjusted under 35 U.S.C. 154(b) by 0 days.

(21) Appl. No.: 10/097,700

(22) Filed: Mar. 12, 2002

(51) Int. Cl.$^7$ ................................................. G01N 23/04
(52) U.S. Cl. ........................................... 378/90; 378/57
(58) Field of Search ............................... 378/57, 86, 87, 378/88, 89, 90

(56) References Cited

U.S. PATENT DOCUMENTS

| | | | |
|---|---|---|---|
| 3,678,278 A | 7/1972 | Peil ............................ 250/108 |
| 3,780,291 A | 12/1973 | Stein et al. .................. 250/363 |
| 3,790,799 A | 2/1974 | Stein et al. .................. 250/363 |
| 3,843,881 A | 10/1974 | Barton, Jr. et al. .......... 250/269 |
| 3,884,816 A | 5/1975 | Takahashi .................... 250/359 |
| 3,919,467 A | 11/1975 | Peugeot ....................... 178/6.8 |
| 3,924,064 A | 12/1975 | Nomura et al. ............... 178/6.8 |
| 4,020,346 A | 4/1977 | Dennis ........................ 250/358 |
| 4,031,545 A | 6/1977 | Stein et al. .................. 358/108 |
| 4,047,035 A | 9/1977 | Dennhoven et al. .......... 250/355 |
| 4,070,576 A | 1/1978 | Cobb .......................... 250/303 |
| 4,112,301 A | 9/1978 | Annis et al. ................. 250/364 |
| 4,139,771 A | 2/1979 | Dennhoven et al. .......... 250/408 |
| 4,160,165 A | 7/1979 | McCombs et al. ............ 250/354 |
| 4,179,100 A | 12/1979 | Sashin et al. ................ 250/416 |
| 4,196,352 A | 4/1980 | Berninger et al. ............ 250/445 |
| 4,200,800 A | 4/1980 | Swift .......................... 250/445 |
| 4,228,357 A | 10/1980 | Annis .......................... 250/445 |
| 4,298,800 A | 11/1981 | Goldman ..................... 250/445 |
| 4,303,830 A | 12/1981 | Heinzelmann et al. ........ 250/445 |
| 4,349,739 A | 9/1982 | Annis ........................... 378/99 |
| 4,366,382 A | 12/1982 | Kotowski ...................... 378/57 |
| 4,366,576 A | 12/1982 | Annis ......................... 378/146 |
| 4,389,729 A | 6/1983 | Stein ............................ 378/99 |
| 4,414,682 A | 11/1983 | Annis et al. ................. 378/146 |
| 4,422,177 A | 12/1983 | Mastronardi et al. .......... 378/17 |
| 4,426,721 A | 1/1984 | Wang ........................... 378/99 |
| 4,454,605 A | 6/1984 | DeLucia ....................... 378/57 |
| 4,472,822 A | 9/1984 | Swift ........................... 378/10 |

(List continued on next page.)

OTHER PUBLICATIONS

Nicholas Tsoulfanidis. Measurement and Detection of Radiation, second edition (Washington, D. C.: Taylor & Francis, 1995).*

"Passenger Screening Technologies," Airline Passenger Security Screening, pp. 13–21.

Bossi, et al., "Backscatter X–Ray Imaging", Materials Evaluation/46/Oct. 1988.

(List continued on next page.)

*Primary Examiner*—Edward J. Glick
*Assistant Examiner*—Allen C. Ho
(74) *Attorney, Agent, or Firm*—Thelen Reid & Priest LLP; Steven J. Robbins (57) ABSTRACT

The present invention provides for an apparatus and method for use in a system with an x-ray source to produce a pencil beam of x-rays to scan an object and a first detector providing a value representative of the intensity of the x-rays scattered from the object to produce a scattered image having a second detector disposed opposite the first detector to provide a value representative of the intensity of the x-rays passing directly from the x-ray source to the second detector; a processor coupled to the system to receive information specifying a position of the pencil beam of x-rays, the processor also coupled to second detector to produce a shadow image formed of pixels indicating the intensity value measured by the second detector for a plurality of positions of the pencil beam of x-rays; and combining the scattered and shadow image to produce a composite image.

48 Claims, 6 Drawing Sheets

U.S. PATENT DOCUMENTS

| | | | |
|---|---|---|---|
| 4,503,332 A | 3/1985 | Annis | 250/368 |
| 4,514,691 A | 4/1985 | De Los Santos et al. | 324/301 |
| 4,535,245 A | 8/1985 | Zonneveld et al. | 250/385 |
| 4,736,401 A | 4/1988 | Donges et al. | 378/146 |
| 4,756,015 A | 7/1988 | Doenges et al. | 378/57 |
| 4,759,047 A | 7/1988 | Donges et al. | 378/57 |
| 4,768,214 A | 8/1988 | Bjorkholm | 378/87 |
| 4,783,794 A | 11/1988 | Dietrich | 378/57 |
| 4,799,247 A | 1/1989 | Annis et al. | 378/87 |
| 4,809,312 A | 2/1989 | Annis | 378/146 |
| 4,817,121 A | 3/1989 | Shimizu et al. | 378/57 |
| 4,819,256 A | 4/1989 | Annis et al. | 378/87 |
| 4,825,454 A | 4/1989 | Annis et al. | 378/87 |
| 4,839,913 A | 6/1989 | Annis et al. | 378/44 |
| 4,845,769 A | 7/1989 | Burstein et al. | 378/58 |
| 4,870,670 A * | 9/1989 | Geus | 378/87 |
| 4,884,289 A * | 11/1989 | Glockmann et al. | 378/57 |
| 4,893,015 A | 1/1990 | Kubierschky et al. | 250/369 |
| 4,974,247 A | 11/1990 | Friddell | 378/90 |
| 5,022,062 A | 6/1991 | Annis | 378/86 |
| 5,033,073 A | 7/1991 | Friddell | 378/146 |
| 5,044,002 A | 8/1991 | Stein | 378/54 |
| 5,084,619 A | 1/1992 | Pfeiler et al. | 250/327.2 |
| 5,127,030 A | 6/1992 | Annis et al. | 378/150 |
| 5,132,995 A | 7/1992 | Stein | 378/56 |
| 5,156,270 A | 10/1992 | Kachel et al. | 206/451 |
| 5,179,581 A | 1/1993 | Annis | 378/57 |
| 5,181,234 A | 1/1993 | Smith | 378/87 |
| 5,224,144 A | 6/1993 | Annis | 378/146 |
| 5,247,561 A | 9/1993 | Kotowski et al. | 378/87 |
| 5,253,283 A | 10/1993 | Annis et al. | 378/100 |
| 5,313,511 A | 5/1994 | Annis et al. | 378/87 |
| 5,579,360 A * | 11/1996 | Abdel-Mottaleb | 378/37 |
| 5,600,700 A | 2/1997 | Krug et al. | 378/57 |
| 5,642,394 A | 6/1997 | Rothschild | 378/57 |
| 5,666,393 A * | 9/1997 | Annis | 378/57 |
| 5,699,400 A | 12/1997 | Lee et al. | 378/57 |
| 5,764,683 A | 6/1998 | Swift et al. | 378/57 |
| 5,796,110 A * | 8/1998 | An et al. | 250/385.1 |
| 5,966,422 A | 10/1999 | Dafni et al. | 378/9 |
| 5,974,111 A | 10/1999 | Krug et al. | 378/57 |
| 6,018,562 A | 1/2000 | Willson | 378/9 |
| 6,094,472 A | 7/2000 | Smith | 378/86 |
| 6,278,115 B1 * | 8/2001 | Annis et al. | 250/363.01 |
| 6,546,072 B1 * | 4/2003 | Chalmers | 378/57 |

OTHER PUBLICATIONS

Gregory, William, "Medical X–Ray Measuring Device Finds Use in Explosive Detection", Aviation Week & Space Technology, vol. 124, No. 17, Apr. 28, 1986.

Gustafsson, et al., "X–Ray Spectrophotometry for Bone–Mineral Determinations", Medical and Biological Engineering; pp. 113–118, Jan. 1974.

Norland Corp., The Norland Dichromatic Bone Densitometer, Advanced Technology for Axial Bone Analysis.

Osteometer Presents: DTX–100 Single Energy X–Ray Bone Densitometer.

PerkinElmer Instruments, "Z–Scan7", printed from http://instruments.perkinelmer.com/products/catalog/prodcuts/prod81.asp (2000).

"New X–Ray System Exposes Unseen Threats", Security World, May 1986.

Stein, et al., "Flying Spot X–ray Imaging Systems", American Science & Engineering, Inc., pp. 137–142, 1972.

Towe, et al., "X–Ray Compton Scatter Imaging Using a High Speed Flying Spot X–Ray Tube" IEEE Transactions on Biomedical Engineering, vol. BME–28, No. 10 Oct. 1981.

Bjorkholm, Paul J., "An X–Ray Inspection System For Detection of Explosives on Personnel", ASE–5249–I vol. I of II (58 pages).

* cited by examiner

X-RAY IMAGING SYSTEM WITH ACTIVE DETECTOR

FIELD OF THE INVENTION

The present invention relates to the general field of radiant energy imaging systems, and specifically to systems and techniques for detecting concealed items on or in objects.

BACKGROUND OF THE INVENTION

Security systems are limited in their ability to detect contraband, weapons, explosives, and other dangerous objects concealed under a person's clothing or in an object, such as a box or bag. Metal detectors and chemical sniffers are commonly used for the detection of large metal objects and some kinds of explosives, however, a wide range of dangerous objects exist that cannot be detected with these devices. Plastic and ceramic weapons developed by modern technology increase the types of non-metallic objects that security personnel are required to detect. The alternative of manual searching of subjects is slow, inconvenient, and would not be well tolerated by the general public, especially as a standard procedure in, for example, airports.

Radiation exposure is an important consideration in x-ray concealed object detection systems. The United States National Council on Radiation Protection (NCRP), in NCRP Report No. 91, "Recommendations on Limits for Exposure to Ionizing Radiation", 1987, addresses this issue. In this report, the NCRP states that a radiation exposure of less than 1000 microRem per year in excess of environmental levels is negligible, and efforts are not warranted at reducing the level further. Persons employed in high security or secured facilities, or those who frequently travel by airlines, may be subjected to many hundred security examinations per year. A yearly radiation exposure limit of 1000 microRem safely permits a single scan exposure within the range of 1 to 10 microRem for the general public. In accordance with the NCRP recommendations, radiation levels significantly higher than this may present some health risk.

Known prior art x-ray systems have limitations in their design and method which prohibit them from achieving the low dose and high image quality that are prerequisites to commercial acceptance. For example, radiant energy imaging systems that detect concealed objects carried on or in an object often scan pencil beam of x-rays through the object where the beam is transmitted or absorbed depending upon the concealed object, if any. A detector may be scanned vertically behind the object in step with the pencil beam to collect the transmitted x-rays.

Figure 1:
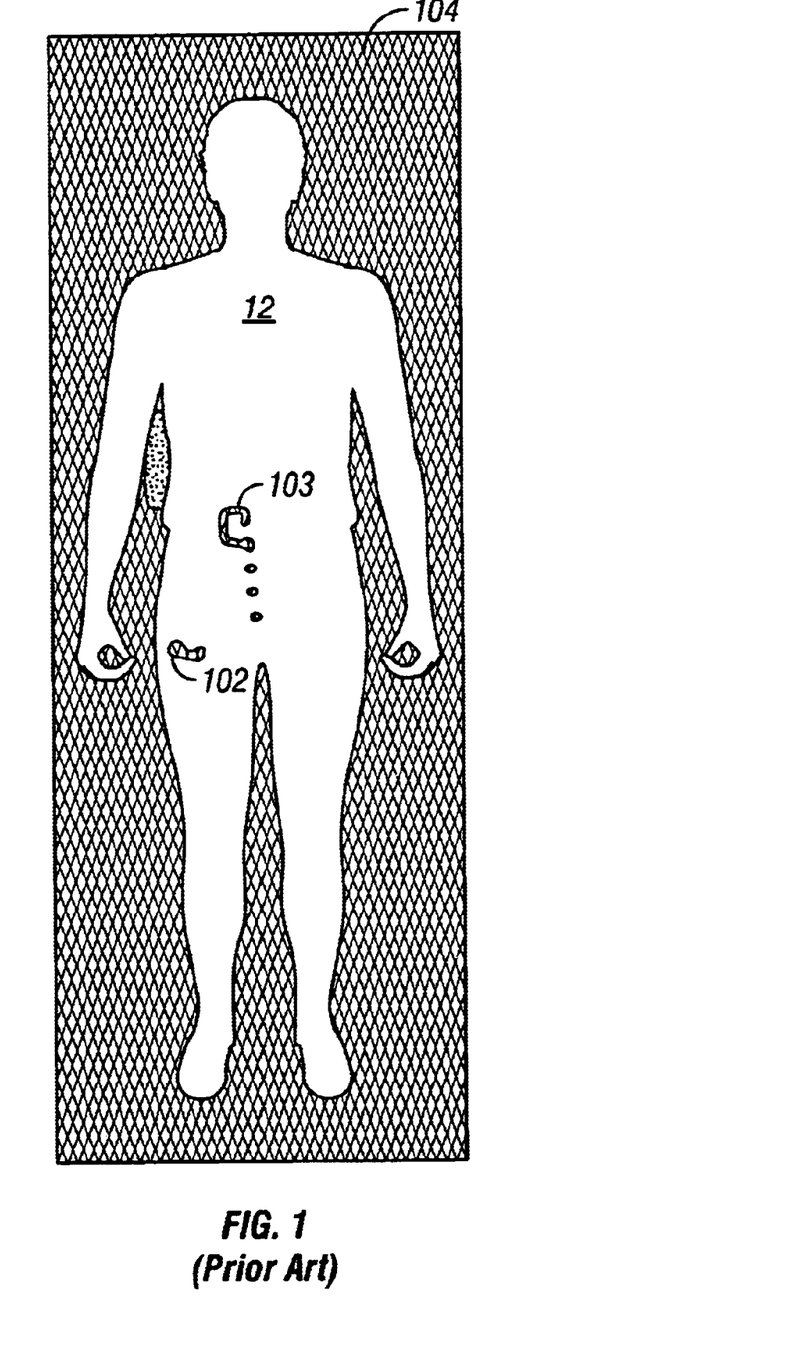
FIG. 1 is a scan image created by an x-ray imaging system in accordance with the prior art.

U.S. Pat. No. 5,181,234 (the '234 patent), herein incorporated by reference as if set forth fully herein, discloses an imaging system which does not require x-rays to be scanned through the object. The '234 patent discloses an imaging apparatus where a narrow pencil beam of x-ray radiation is scanned over the object whereby x-rays that strike low atomic number materials, such as soft tissue, are scattered (i.e. reflected) back toward the apparatus. In comparison, x-rays that strike metal are mostly absorbed and generate very little scatter. Moreover, x-rays that do not strike the object are not captured or scattered back toward the apparatus since the x-rays continue until absorbed or scattered by items further behind the object. Detectors within the apparatus capture the scattered x-rays and generate a corresponding image. For example, as shown in FIG. 1, the vast majority of the body 12 appears light, as a result of the soft tissue generating significant back scatter of x-rays. Metals such as coins in the pocket 102 and belt buckle 103 appear dark due to their absorption of the x-rays. The background 104 around the body is also dark since there is nothing to scatter the x-rays back to the detector.

Figure 2:
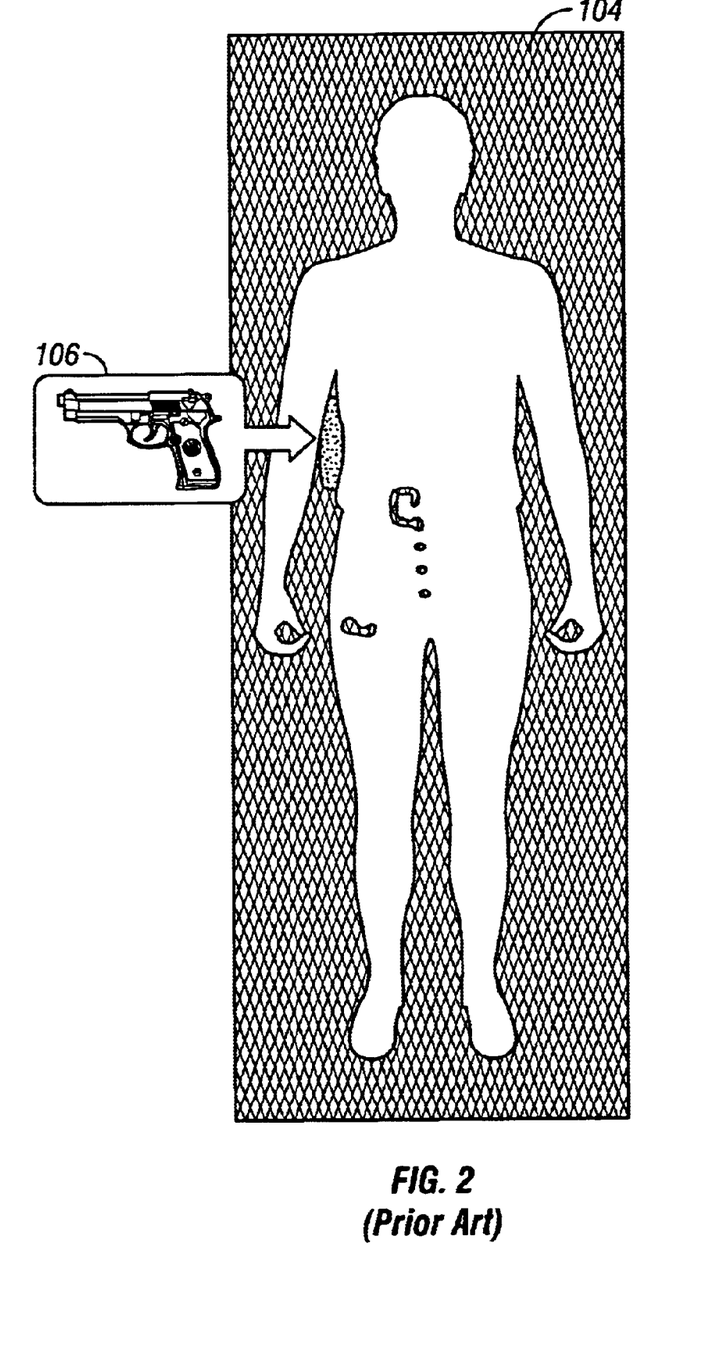
FIG. 2 is a scan image illustrating potential disadvantages of imaging systems in accordance with the prior art.

As shown in FIG. 2, a potential disadvantage of this approach is the difficulty in detecting metal objects that appear in front of or against the background 104 and not in front of the body 12. FIG. 2 shows a metal handgun 106 concealed under the subject's 12 arm. The handgun 106 is virtually impossible to detect in this view since both the handgun 106 and the background 104 appear dark. People may also hang or wear metal objects on their sleeves or pant legs, which would be difficult to detect since they would appear dark and be displayed against the dark background.

Another potential disadvantage of the prior art is that it provides no mechanism to control the x-rays not scattered or absorbed by the object. Currently, the x-rays not scattered or absorbed by the object continue until absorbed or scattered by other items beyond the object. Thus, no objects or persons should be within six to fifteen feet of the apparatus otherwise the person or object will be unnecessarily exposed to the x-rays and may even appear in the image.

Thus, there is a need for an apparatus that would overcome the disadvantages of prior art x-ray systems and allow for the detection of concealed objects appearing against the background. There is also a need for a way to control x-rays that are not scattered or absorbed by the object to protect other persons from unnecessary exposure to the x-rays and to prevent image degradation.

BRIEF DESCRIPTION OF THE INVENTION

The present invention provides for an apparatus and method for use in a system with an x-ray source to produce a pencil beam of x-rays to scan an object and a first detector providing a value representative of the intensity of the x-rays scattered from the object to produce a scattered image; having a second detector disposed opposite the first detector to provide a value representative of the intensity of the x-rays passing directly from the x-ray source to the second detector; a processor coupled to the system to receive information specifying a position of the pencil beam of x-rays, the processor also coupled to second detector to produce a shadow image formed of pixels indicating the intensity value measured by the second detector for a plurality of positions of the pencil beam of x-rays; and combining the scattered and shadow image to produce a composite image.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings.

DETAILED DESCRIPTION

Embodiments of the present invention are described herein in the context of a x-ray imaging system with active detector. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

In accordance with the present invention, the components, process steps, and/or data structures may be implemented using various types of operating systems, computing platforms, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein.

Figure 3:
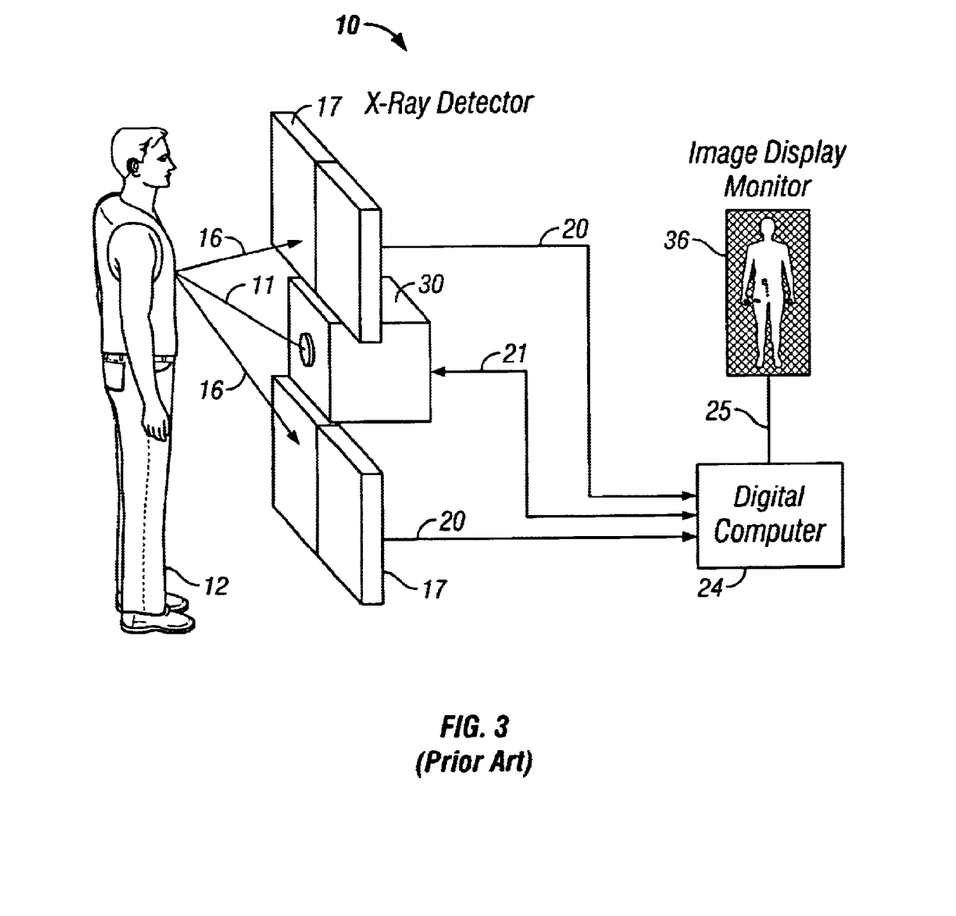
FIG. 3 is a diagrammatic view of an imaging system in accordance with the prior art.

One embodiment of the present invention will be described with reference to the x-ray detector of the '234 patent. However, those of ordinary skill in the art will now realize that the present invention may be used with other x-ray detectors known in the art. FIG. 3 shows the imaging system 10 scanning a pencil beam 11 of x-rays over the surface of the body 12 of the person being examined. X-rays 16 scattered or reflected from the body 12 are detected by x-ray sensitive detectors 17 positioned on the same side of the subject as the x-ray pencil beam source 30. The detectors 17 are positioned for substantially uniform x-ray detection on all sides of the incident x-ray beam. The electronic signals 20 produced from the detectors 17 and synchronization signals 21 from the x-ray source 30 are routed into the digital computer 24. The computer 24 generates a scatter image 25 on a monitor (screen) 36 wherein the intensity at each point in the display corresponds to the relative intensity of the detected scattered x-rays. The digitized scatter image preferably consists of 480 rows by 160 columns with 8 bits per pixel.

As described in detail in the '234 patent, x-rays interact with matter in two ways: Compton scattering and the photoelectric effect. An x-ray interacting by Compton scattering is deflected out of the original x-ray beam creating back scattered radiation. The photoelectric effect, in comparison, absorbs x-rays and thus reduces the level of back scatter. At low atomic numbers and high energies, Compton scattering is more likely to occur than the photoelectric effect. This gives rise to a large amount of scatter and the relatively high reflectance. At higher atomic numbers and lower x-ray energies, the photoelectric effect absorbs more of the x-rays resulting in less scatter and the low reflectance.

Figure 4:
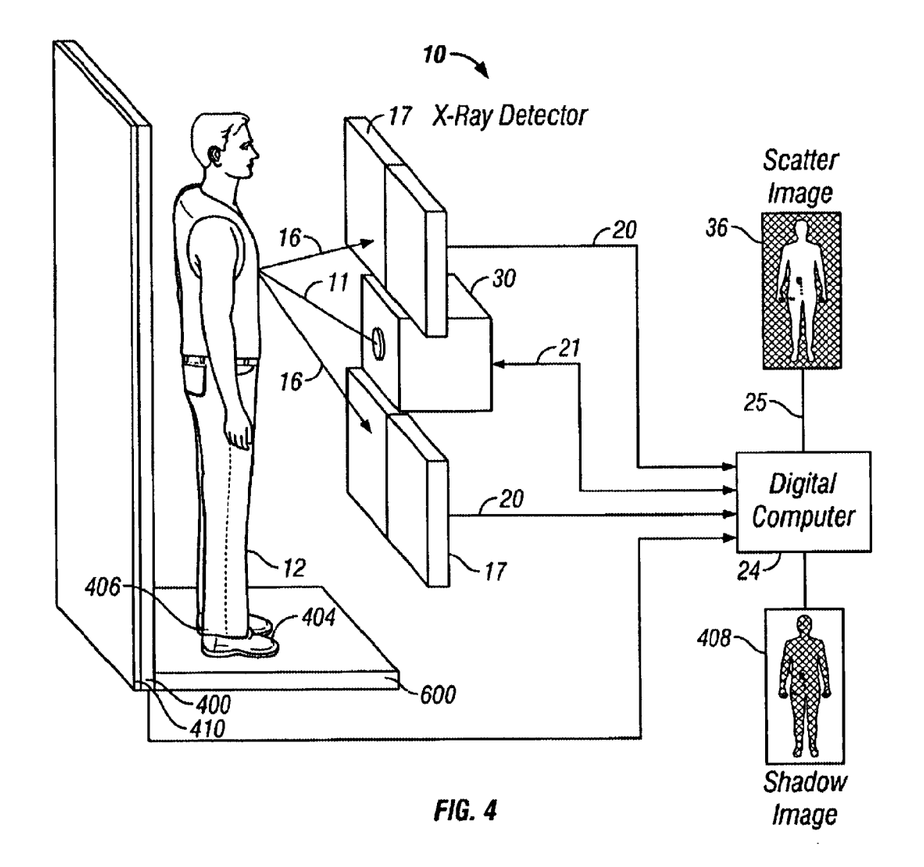
FIG. 4 is a diagrammatic view of an x-ray scanning system in accordance with the present invention.

As shown in FIGS. 1 and 2, x-rays not scattered by the body 12 or object continue past the body 12 and are not scattered back to the detector 17 thereby creating a dark background 104. To overcome the disadvantages of having the dark background 104, an x-ray detector panel 400 is positioned behind the object 12 as shown in FIG. 4. The panel 400 has an active area that is approximately 48 inches wide, by 80 inches high. Those of ordinary skill in the art will now realize that other dimensions may be used depending upon the application. The detector panel 400 may be between two to six feet from the detector 17, but is preferably three feet from the detector 17. For non-human scanning applications, other distances may be used as appropriate.

It will now be understood by those of ordinary skill in the art that the panel 400 may be placed in different alternative positions. As shown in FIG. 4, a floor panel 600 may be placed underneath the person 12 or object being scanned to detect, for example, objects in the shoes 404, on the legs 406, or feet of the person being scanned. In another alternative embodiment, the panel may also extend outwardly from the sides and the top. Those of ordinary skill in the art will now realize that the panel may be formed of any shape such as a square, semi-circle, or any other shape around the person or object scanned.

In one embodiment, the detector panel 400 may be comprised of one or more gas filled ionization chambers capable of transforming incident radiation into an electronic signal. The gas filled ionization chambers produce hole-electron pairs in response to x-rays impinging on the rear detector panel 400. The hole-electron pairs then produce an electrical signal that is sent to the computer 24 to produce a shadow image 408. The electrical signal is then converted into a digital image in the same manner as described in the '234 patent. Although the scatter image 36 is preferably comprised of 480 rows by 160 columns with 8 bits per pixel, the shadow image 408 of the present invention consists of 480 rows by 160 columns with only one bit per pixel. The pixels of the shadow image 408 thereby represent one of two intensity values. One of the intensity values represents that the x-ray beam 11 directed at the corresponding position of the detector panel 400 impinged the detector panel 400. In this case, the pixel value represents the "background" of the shadow image 408 since the x-ray did not scatter from the object 12. The other intensity value represents that the x-ray beam 11 did not impinge the rear detector panel 400. That is, the pixel value represents the "body" of the shadow image 408 since the x-rays were either scattered from the object 12 or absorbed by high atomic number materials.

In another embodiment, the panel 400 may comprise any type of scintillation material capable of transforming incident radiation into electronic signals that are known to those of ordinary skill in the art such as a fluorescent screen or a plastic scintillator. The scintillation material gives off light when struck by x-rays, which is then read out by a light detector. The light detector may be any type of detector known to those of ordinary skill in the art such as a photodiode or a photomultiplier tube. The light detectors are mounted within the panel 400 to produce the electronic signals in response to the light emission of the scintillation material, as it is being scanned by the x-ray beam 11. The electronic signals are converted into a digital shadow image 408 in the same manner as described in the '234 patent. Although the scatter image 36 preferably consists of 480 rows by 160 columns with 8 bits per pixel, the shadow image 408 of the present invention consists of 480 rows by 160 columns with only one bit per pixel. One of the intensity values represents that the x-ray beam 11 directed at the corresponding position of the panel 400 impinged the panel 400. That is, the pixel value represents the "background" of the shadow image since the x-ray did not scatter from the object 12. The other intensity value represents that the x-ray beam 11 did not impinge the detector 400. That is, the pixel value represents the "body" of the shadow image 408 since the x-rays were either scattered from the object 12 or absorbed by high atomic number materials.

Figure 5:
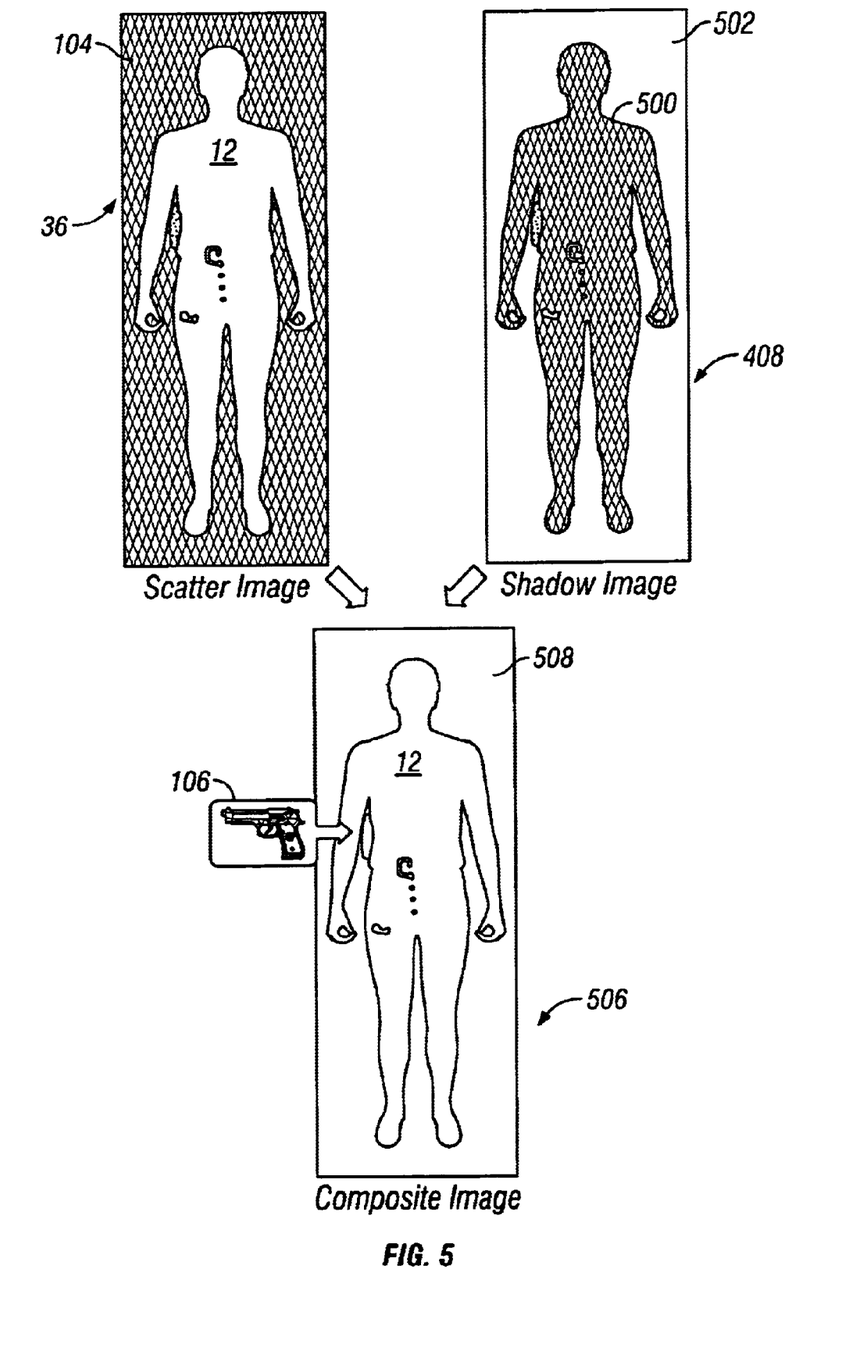
FIG. 5 are scan images created in accordance with the present invention.

The present invention utilizes low energy x-rays that are only capable of penetrating a short distance into a body. In particular, none of the x-rays are able to penetrate completely through the subject's body. This means that the x-ray image reaching the rear detector is a "shadow" of the subject. As illustrated in FIG. 5, the shadow image 408 seen by the rear detector is composed of only two regions—the shadow 500 of the subject that appears dark, and the background 502 around the subject that appears light as a result of the detection of the unattenuated x-ray beam.

The present invention is based upon the way that high atomic number materials such as metal appear in both the scatter image 36 and the shadow image 408. In the scatter image 36, metal appears the same as the background 104, but different from the body 12. However, in the shadow image 408, high atomic number materials, such as metal, appears the same as the body 500 but different from the background 502. Thus, a combination of the two images will allow high atomic number materials such as metal to be easily detected, as shown in the composite image 506. The composite image 506 comprises the intensity values from the shadow image 408 representing that the x-ray beam impinged the rear detector panel. That is, the composite image comprises the "background" 502 of the shadow image 408. The composite image 506 also comprises the intensity values from the scattered image 36 if the x-rays were scattered back to the detector 17. That is, the composite image also comprises the values representative of the intensity of the x-rays scattered from the object. In the composite image 506, the background 508 of the image is no longer dark, but is displayed as an intermediate shade of gray or some non-gray color. Moreover, the metal gun 106 is visibly noticeable since it appears as a dark color. This allows any high Z materials, such as metal, to be visible whether it is against the background 508 or the body 12.

As shown in FIG. 4, the present invention may also have a radiation shield 410 coupled to the panel 400 to capture any x-rays 11 that may pass through the panel 400. This will ensure that any person behind the panel 400 will not be inadvertently exposed to x-rays. Moreover, the radiation shield 410 will ensure that objects behind the panel 400 will not be reproduced in the images 36 and 408. The radiation shield 410 may be made of any x-ray absorbing material such as steel or lead and be a few percent of the thickness of the panel 400.

Figure 6:
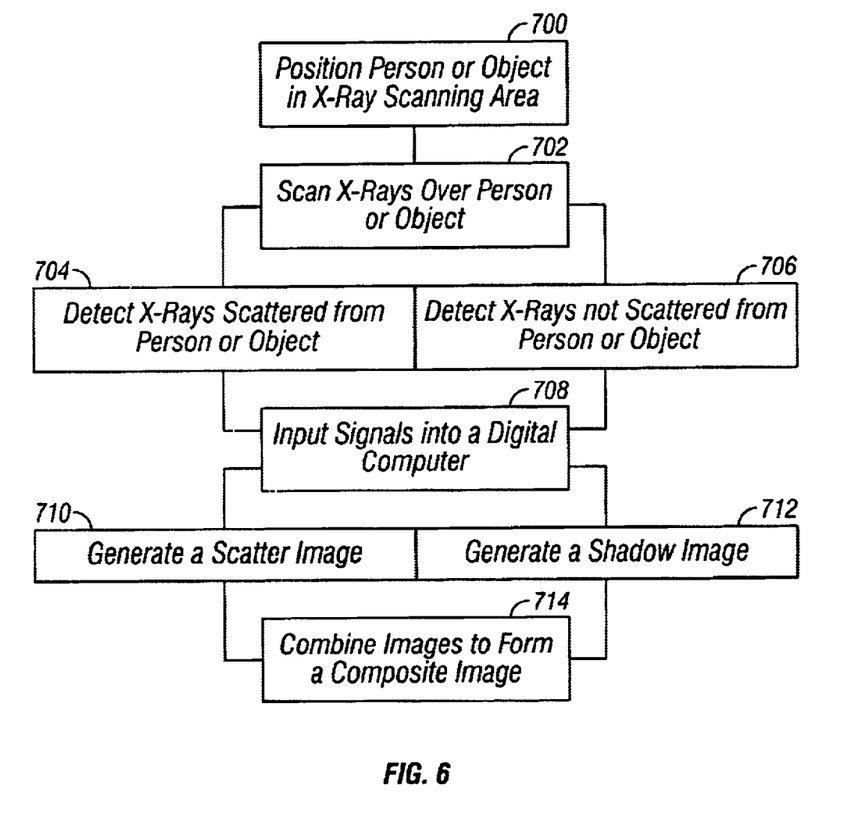
FIG. 6 is a flow diagram illustrating a method in accordance with the present invention.

The present invention also provides a method for detecting concealed items on or in an object. An object or body is positioned in the x-ray scanning area 700 and a pencil beam of x-rays is scanned over the surface of the body or object 702 being examined. X-rays scattered or reflected from the body are detected 704 by x-ray sensitive detectors. The detectors are positioned for substantially uniform x-ray detection on all sides of the incident x-ray beam. The electronic signals produced from the detectors and synchronization signals from the x-ray source are inputted into the digital computer 708. The computer generates a scattered image display 710 on a monitor (screen) wherein the intensity at each point in the display corresponds to the relative intensity of the detected scattered x-rays.

X-rays not scattered or reflected from the body are detected 706 by an x-ray detector panel positioned behind the object. The panel has an active area that is approximately forty-eight inches wide by eighty inches high. Those of ordinary skill in the art will now realize that other dimensions may be used depending upon the application. The detector panel may be between two to six feet from the detector, but is preferably three feet from the detector. For non-human scanning applications, other distances may be used as appropriate.

It will now be understood by those of ordinary skill in the art that the panel may be placed in different alternative positions. A floor panel may be placed underneath the person or object being scanned to detect, for example, objects in the shoes or on the legs or feet of the person being scanned. In another alternative embodiment, the panel may also extend outwardly from the sides and the top. Those of ordinary skill in the art will now realize that the panel may be formed of any shape such as a square, semi-circle, or any other shape around the person or object scanned.

In one embodiment, the detector panel may be comprised of one or more gas filled ionization chambers capable of transforming incident radiation into an electronic signal. The gas filled ionization chambers produce hole-electron pairs in response to x-rays impinging on the rear detector panel. The hole-electron pairs then produce an electrical signal that is sent to the computer 708 to produce a shadow image 712. The electrical signal is then converted into a digital image in the same manner as described in the '234 patent. Although the scatter image preferably consists of 480 rows by 160 columns with 8 bits per pixel, the shadow image of the present invention consists of 480 rows by 160 columns with only one bit per pixel. The pixels of the shadow image thereby represent one of two intensity values. One of the intensity values represents that the x-ray beam directed at the corresponding position of the detector panel impinged the panel. In this case, the pixel value represents the "background" of the shadow image since the x-ray did not scatter from the object. The other intensity value represents that the x-ray beam did not impinge the panel. That is, the pixel value represents the "body" of the shadow image since the x-rays were either scattered from the object or absorbed by high atomic number materials.

In another embodiment, the panel may comprise any type of scintillation material capable of transforming incident radiation into electronic signals that are known to those of ordinary skill in the art such as a fluorescent screen or a plastic scintillator. The scintillation material gives off light when struck by x-rays, which is then read out by a light detector. The light detector may be any type of detector known to those of ordinary skill in the art such as a photodiode or a photomultiplier tube. The light detectors are mounted within the panel to produce the electronic signals in response to the light emission of the scintillation material, as it is being scanned by the x-ray beam. The electronic signals are converted into a digital shadow image in the same manner as described in the '234 patent. Although the scatter image preferably consists of 480 rows by 160 columns with 8 bits per pixel, the shadow image of the present invention consists of 480 rows by 160 columns with only one bit per pixel. One of the intensity values represents that the x-ray beam directed at the corresponding position of the panel impinged the panel. In this case, the pixel value represents the "background" of the shadow image since the x-ray did not scatter from the object. The other intensity value represents that the x-ray beam did not impinge the panel. That is, the pixel value represents the "body" of the shadow image since the x-rays were either scattered from the object or absorbed by high atomic number materials.

The present invention utilizes low energy x-rays that are only capable of penetrating a short distance into a body. In particular, none of the x-rays are able to penetrate completely through the subject's body. This means that the x-ray image reaching the rear detector is a "shadow" of the subject. The shadow image seen by the rear detector is composed of only two regions—the shadow of the subject that appears dark, and the background around the subject that appears light as a result of the detection of the unattenuated x-ray beam.

The present invention is based upon the way that high atomic number materials such as metal appear in both the scatter image and the shadow image. In the scatter image, metal appears the same as the background, but different from the body. However, in the shadow image, high atomic number materials, such as metal, appears the same as the body but different from the background. Thus, a combination of the two images 714 will allow high atomic number materials such as metal to be easily detected. The composite image of both the scattered and shadow images comprise the intensity values from the shadow image representing that the x-ray beam impinged the panel. In this case, the composite image comprises the "background" of the shadow image. The composite image also comprises the intensity values from the scattered image if the x-rays were scattered back to the detector. That is, the composite image also comprises the values representative of the intensity of the x-rays scattered from the object. The background of the image is no longer dark, but is displayed as an intermediate shade of gray or some non-gray color. Moreover, the metal gun is visibly noticeable since it appears as a dark color. This allows any high Z materials, such as metal, to be visible whether it is against the background or the body.

The present invention may also have a radiation shield coupled to the panel to capture any x-rays that may pass through the panel. This will ensure that any person behind the panel will not be inadvertently exposed to x-rays. Moreover, the radiation shield will ensure that objects behind the panel will not be reproduced in the images. The radiation shield may be made of any x-ray absorbing material such as steel or lead and be a few percent of the thickness of the panel.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. An apparatus for use in a system having an x-ray source to produce a pencil beam of x-rays to scan an object and a first detector providing a value representative of the intensity of the x-rays scattered from the object to produce a scattered image, said apparatus comprising:

a second detector disposed opposite said first detector, said second detector providing a value representative of the intensity of the x-rays passing directly from said x-ray source to said second detector; and a processor coupled to the system and receiving therefrom information specifying a position of the pencil beam of x-rays, the processor also coupled to said second detector and producing a shadow image formed of pixels that are not blocked by the object and which indicate an intensity value measured by said second detector for a plurality of positions of said pencil beam of x-rays.

2. The apparatus in accordance with claim 1 wherein said pixels are limited to representing one of two intensity values.

3. The apparatus in accordance with claim 2 wherein one of said two intensity values represents that the x-ray beam directed at the corresponding position of said second detector was detected to have impinged said second detector and wherein the other of said two values represents that the x-ray beam was not detected to have impinged said second detector.

4. The apparatus of claim 1 wherein said second detector is disposed about 2 to 6 feet from said x-ray source.

5. The apparatus of claim 1 wherein said second detector comprises a plurality of gas filled ionization chambers.

6. The apparatus of claim 1 wheren said second detector comprises a scintillation material and a light detector.

7. The apparatus of claim 6 wherein said scintillation material comprises a fluorescent screen.

8. The apparatus of claim 6 wherein said scintillation material comprises a plastic scintillator.

9. The apparatus of claim 6 wherein said light detector comprises a photomultiplier tube.

10. The apparatus of claim 6 wherein said light detector comprises a photodiode.

11. The apparatus of claim 1 further comprising a radiation shield coupled to said second detector.

12. The apparatus of claim 11 wherein said radiation shield comprises an x-ray absorbing material.

13. The apparatus of claim 12 wheren said x-ray absorbing material is steel.

14. The apparatus of claim 12 wherein said x-ray absorbing material is lead.

15. The apparatus of claim 1 wherein said shadow image is capable of being combined with said scattered image to form a composite image.

16. The apparatus of claim 15 wherein said composite image comprises the intensity value from said shadow image where the x-ray beam impinged said second detector, and wherein said composite image comprises the value representative of the intensity of the x-rays scattered from the object where the x-ray beam did not impinge said second detector.

17. A method for detecting concealed items on or in an object in a system having an x-ray source to produce a pencil bean of x-rays to scan the object and a first detector providing a value representative of the intensity of the x-rays scattered from the object to produce a scattered image, said method comprising:

detecting x-rays that pass unscattered from said x-ray source to a second detector disposed opposite said first detector;

forming a signal in response to said detection of x-rays;

receiving information from said system to a processor specifying a position of the pencil beam of x-rays; and producing a shadow image formed of pixels that are not blocked by the object and which indicate an intensity value measured by said second detector for a plurality of positions of said pencil beam of x-rays.

18. The method in accordance with claim 17 wherein said pixels are limited to representing one of two intensity values.

19. The method in accordance with claim 18 wherein one of said two intensity values represents that the x-ray beam directed at the corresponding position of said second detector was detected to have impinged said second detector and wherein the other of said two values represents that the x-ray beam was not detected to have impinged said second detector.

20. The method of claim 17 further comprising disposing said second detector about 2 to 6 feet from said x-ray source.

21. The method of claim 17 wherein said second detector comprises a plurality of gas filled ionization chambers.

22. The method of claim 17 wherein said second detector comprises a scintillation material and a light detector.

23. The method of claim 22 wherein said scintillation material comprises a fluorescent screen.

24. The method of claim 22 wherein said scintillation material comprises a plastic scintillator.

25. The method of claim 22 wherein said light detector comprises a photomultiplier tube.

26. The method of claim 22 wherein said light detector comprises a photodiode.

27. The method of claim 17 further comprising coupling a radiation shield to said second detector.

28. The method of claim 27 wherein said radiation shield comprises an x-ray absorbing material.

29. The method of claim 28 wherein said x-ray absorbing material is steel.

30. The method of claim 28 wherein said x-ray absorbing material is lead.

31. The method of claim 17 further comprising combining said shadow image with said scattered image to form a composite image.

32. The method of claim 31 wherein said composite image comprises the intensity value from said shadow image where the x-ray beam impinged said second detector, and wherein said composite image comprises the value representative of the intensity of the x-rays scattered from the object where the x-ray beam did not impinge said second detector.

33. A program storage device readable by a machine, tangibly embodying a program of instructions executable by the machine to perform a method for detecting concealed items on or in an object in a system having an x-ray source to produce a pencil beam of x-rays to scan the object and a first detector providing a value representative of the intensity of the x-rays scattered from the object to produce a scattered image, said method comprising:

detecting x-rays that pass unscattered from said x-ray source to a second detector disposed opposite said first detector;

forming a signal in response to said detection of x-rays;

receiving information from said system to a processor specifying a position of the pencil beam of x-rays; and producing a shadow image formed of pixels that are not blocked by the object and which indicate an intensity value measured by said second detector for a plurality of positions of said pencil beam of x-rays.

34. A system for scanning an object, comprising:

an x-ray source to produce a pencil beam of x-rays to scan the object;

a first detector to provide a value representative of the intensity of x-rays scattered from the object;

an image former responsive to said first detector to form a scattered image;

a second detector disposed opposite said first detector, said second detector providing a value representative of an intensity of x-rays passing directly from said x-ray source to said second detector; and a processor coupled to receive information specifying a position of the pencil beam of x-rays, the processor also coupled to said second detector and producing a shadow image formed of pixels that are not blocked by the object and which indicate an intensity value measured by said second detector for a plurality of positions of said pencil beam of x-rays.

35. The system in accordance with claim 34 wherein said pixels are limited to representing one of two intensity values.

36. The system in accordance with claim 35 wherein one of said two intensity values represents that the x-ray beam directed at the corresponding position of said second detector was detected to have impinged said second detector and wherein the other of said two values represents that the x-ray beam was not detected to have impinged said second detector.

37. The system of claim 34 wherein said shadow image is adapted to be combined with said scattered image to form a composite image.

38. The system of claim 37 wherein said composite image comprises the intensity value from said shadow image where the x-ray beam impinged said second detector, and wherein said composite image comprises the value representative of the intensity of the x-rays scattered from the object where the x-ray beam did not impinge said second detector.

39. A system for scanning an object, comprising:

x-ray scanning means for producing a pencil beam of x-rays to scan the object;

scattered x-ray detection means for detecting an intensity of x-rays scattered from the object;

image forming means responsive to said scattered x-ray detection means for forming a scattered image;

direct x-ray detection means disposed opposite said scattered x-ray detection means, said direct x-ray detection means responsive to an intensity of x-rays passing directly from said x-ray source to said direct x-ray detection means; and processor means coupled to receive information specifying a position of the pencil beam of x-rays, said processor means also responsive to said direct x-ray detection means for forming a shadow image formed of pixels that are not blocked by the object and which indicate intensity values measured by said direct x-ray detection means at a plurality of positions of said pencil beam of x-rays.

40. The system in accordance with claim 39 wherein said pixels are limited to representing one of two intensity values.

41. The system in accordance with claim 40 wherein one of said two intensity values represents that the beam of x-rays directed at a corresponding position of said direct x-ray detection means was detected to have impinged said direct x-ray detection means and wherein the other of said two values represents that the beam of x-rays was not detected to have impinged said direct x-ray detection means.

42. The system of claim 39 wherein the shadow image is adapted to be combined with said scatted image to form a composite image.

43. The system of claim 42 wherein said composite image comprises the intensity value from said shadow image where the x-ray beam impinged said direct x-ray detection means, and wherein said composite image comprises the value representative of the intensity of the x-rays scattered from the object where the x-ray beam did not impinge said direct x-ray detection means.

44. A method for scanning an object, comprising:

forming a pencil beam of x-rays with an x-ray source;

scanning the object with the pencil beam of x-rays;

detecting an intensity of x-rays scattered from the object;

forming a scattered image in response to said detecting;

measuring an intensity of x-rays passing directly from said x-ray source to a direct x-ray detector; and forming a shadow image of pixels that are not blocked at the object and which indicate intensity values measured by the direct x-ray detector at a plurality of positions of the pencil beam of x-rays.

45. The method in accordance with claim 44 wherein the pixels are limited to representing one of two intensity values.

46. The method in accordance with claim 45 wherein one of the two intensity values represents that the beam of x-rays directed at a corresponding position of the direct x-ray detection means was detected to have impinged said direct x-ray detection means and wherein the other of the two values represents that the beam of x-rays was not detected to have impinged the direct x-ray detector.

47. The method of claim 44, further comprising:

combining the shadow image with the scattered image to form a composite image.

48. The method of claim 47 wherein the composite image comprises the intensity value from the shadow image where the beam of x-rays impinged the direct x-ray detector, and wherein the composite image comprises the value representative of the intensity of the x-rays scattered from the object where the x-ray beam did not impinge the direct x-ray detector.

* * * * *

UNITED STATES PATENT AND TRADEMARK OFFICE
CERTIFICATE OF CORRECTION

PATENT NO.     : 6,665,373 B1
DATED          : December 16, 2003
INVENTOR(S)    : Andreas F. Kotowski and Steven W. Smith It is certified that error appears in the above-identified patent and that said Letters Patent is hereby corrected as shown below:

<u>Column 8,</u>
Lines 23 and 37, replace "wheren" with -- wherein --.
Line 53, replace "bean" with -- beam --.

Signed and Sealed this

Fifteenth Day of June, 2004

JON W. DUDAS
*Acting Director of the United States Patent and Trademark Office*